United States Patent [19]

Tumanov et al.

[11] 4,213,325

[45] Jul. 22, 1980

[54] DEVICE FOR INTRODUCING PARTICLES INTO ANALYZER OF DUSTINESS OF GASEOUS MEDIUM

[76] Inventors: Evgeny S. Tumanov, ulitsa Shelkovichnaya, 184, kv. 48; Nikolai V. Zhamkov, ulitsa Mokhovaya, 33/1; Lev A. Kudryavtsev, ulitsa Shelkovichnaya, 182, kv. 72,, all of Saratov, U.S.S.R.

[21] Appl. No.: 946,029

[22] Filed: Sep. 26, 1978

[51] Int. Cl.² .......................................... G01N 15/00
[52] U.S. Cl. .......................................... 73/1 G; 73/28
[58] Field of Search ...................... 73/28, 1 G, 432 PS; 250/222 PC, 574; 356/246, 335, 336; 235/92 PC

[56] References Cited

U.S. PATENT DOCUMENTS

| 1,900,477 | 3/1933 | Wittemeier | 73/28 |
| 3,495,439 | 2/1970 | Von Brand | 250/222 PC |
| 3,770,351 | 11/1973 | Wyatt | 356/336 |
| 3,926,344 | 12/1975 | Bradley et al. | 222/145 |
| 4,024,407 | 5/1977 | Meric et al. | 250/574 |

FOREIGN PATENT DOCUMENTS 321730  11/1972  U.S.S.R. .

*Primary Examiner*—Stephen A. Kreitman
*Attorney, Agent, or Firm*—Fleit & Jacobson

[57] ABSTRACT

A device for introducing particles into an analyzer of dustiness of a gaseous medium comprises a cell having a transparent cover with a microscope arranged thereabove. A through guide duct is made in a wall of the cell, while provided in the bottom of the latter are a vertical feed duct communicating with the dustiness analyzer and a horizontal channel which is an extension of the through guide duct and intersects the vertical feed duct. The device also comprises a source of a pure gaseous medium which is fed under pressure into the through guide duct wherewith the source communicates.

3 Claims, 1 Drawing Figure

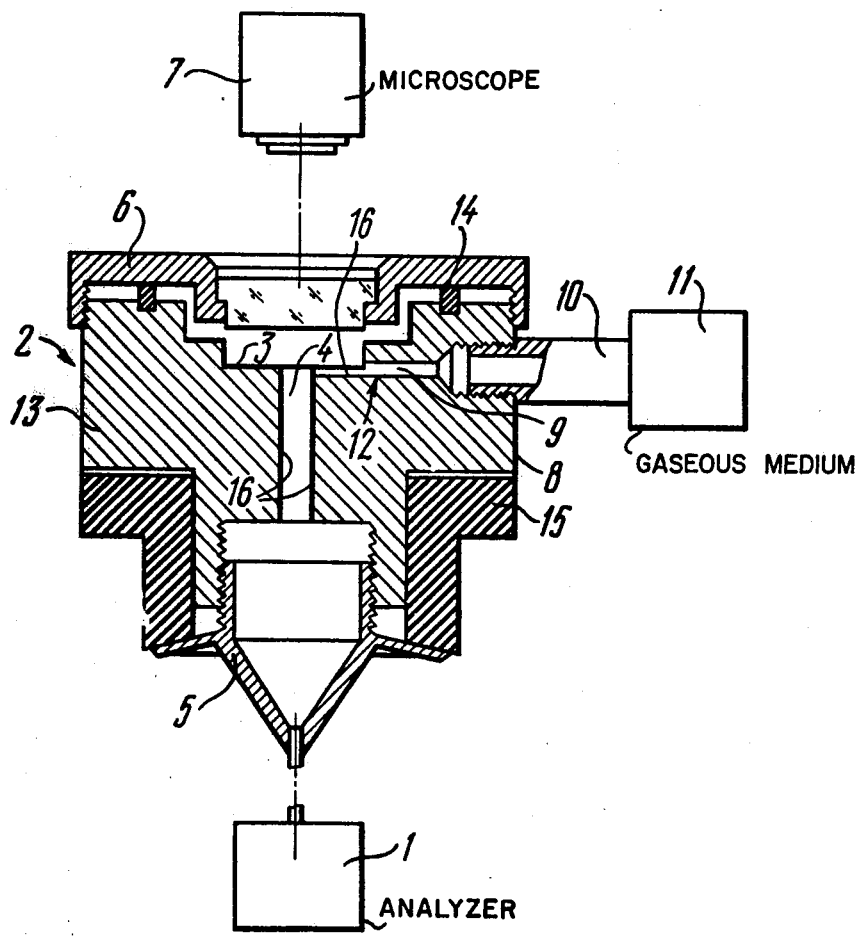

DEVICE FOR INTRODUCING PARTICLES INTO ANALYZER OF DUSTINESS OF GASEOUS MEDIUM

FIELD OF THE INVENTION

The present invention relates to metrology, and more particularly to devices for introducing particles into analyzers of dustiness of a gaseous medium.

The invention can most advantageously be used for determining the intrinsic particle counting error of airborne dust monitors.

BACKGROUND OF THE INVENTION

At present, the predominant trend in aerosol engineering is the development of automatic analyzers of dustiness of gaseous media. Therewith, stringent requirements are imposed on the metrological characteristics of analyzers, particularly, on the particle counting error. This requirement is met by introducing a known quantity of particles into an analyzer, thereby enabling the intrinsic particle counting error of the latter to be determined.

Known in the art is a device for dispensing metered amounts of small-size particles (cf. U.S. Pat. No. 3,926,344; Cl. G01f 11/28), comprising vertical ducts with ports and valves for letting out metered amounts of particles, and vertically arranged measuring tubes having their bottom ends inserted into the vertical ducts and intended for particles to flow therethrough. The measuring tubes determine the measuring volume of particles fo various sizes. The valves arranged above the measuring tubes provide for selective feed of small-size particles into the measuring tubes. The movement of particles in the device and at its outlet is by gravity.

However, in this prior art device, no provision is made for preliminary (prior to letting out) measurement of the number of discrete particles, whereas, in the case where the device is used for calibrating digital aerosol particle counters, this number should be known with a high degree of accuracy.

In addition, the presence of a valve in the outlet duct of the prior art device increases the turbulence of the moving particles, hence, the probability of the same particles being counted several times.

Also known is a device for introducing particles into an analyzer of dustiness of a gaseous medium (cf. USSR Inventor's Certificate No. 321,730; Cl. G01n 15/00), comprising a cell having a vertical feed duct made in its bottom and communicating with the analyzer, and a transparent cover with a microscope positioned thereabove. The device also comprises a luminous flux discriminator with a light source.

However, in this device, one observes in the transparent cell not the particles themselves, but flashes of the light reflected therefrom, which renders particle counting difficult. Moreover, in the prior art device, a plurality of flashes may be seen in the microscope's field of vision, which lowers the accuracy of counting particles.

In addition, both prior art devices lack a transporting medium, which results in an ineffective egress of small particles from the measuring chamber and the outlet duct, which particles are highly adhesive, i.e. the ability of the device to have its measuring chamber and the outlet duct purged from the particles present therein during each operating cycle is poor. Since, in a certain particle size range this factor is of paramount importance, e.g. 25 to 50 microns and smaller, the adhesiveness of particles increases to such an extent that the effective detachment thereof from the surface of the measuring chamber is not only impossible by gravity, but the reguired velocity of the transporting medium (air) is so high that the source of pure air becomes prohibitively cumbersome.

Another disadvantage of the above devices resides in that non-focused outflow of particles from the outlet duct at a low velocity makes the paths of their movement closer to random ones. This introduces an additional error in calibrating analyzers because again the probability of the same particles being counted by the analyzer's sensor several times is high.

SUMMARY OF THE INVENTION

It is an object of the present invention to provide a device for introducing particles into an analyzer of dustiness of a gaseous medium, ensuring high accuracy of counting the introduced particles.

This is attained by that in a device for introducing particles into an analyzer of dustiness of a gaseous medium, comprising a cell having a vertical feed duct made in its bottom and intended for communication with the anlyzer, and a transparent cover with a particle counting microscope positioned thereabove, according to the invention, made in a wall of the cell is a through guide duct, while made in the bottom of the cell is a horizontal channel which is an extension of the through guide duct and intersects the vertical feed duct, and the device is provided with a source of a pure gaseous medium, communicating with the through guide duct and intended to supply the pure gaseous medium, under pressure, into the through guide duct.

Preferably, the inner surfaces of the horizontal channel and the vertical feed duct should have an antiadhesive coating.

The device of the present invention permits introducing a known quantity of particles into an analyzer, which enables one to determine the intrinsic particle counting error of the analyzer.

In addition, in the proposed device, the loss of particles being counted is minimum, which rules out the possibility of any error being introduced by the device for introducing particles into an analyzer of dustiness of a gaseous medium.

BRIEF DESCRIPTION OF THE ACCOMPANYING DRAWING

Other objects and advantages of the present invention will become more apparent from the following detailed description of a specific embodiment thereof, taken in conjunction with the accompanying drawing which is a schematic of a device for introducing particles into an analyzer of dustiness of a gaseous medium, according to the invention (the cell as well as parts of the pure gaseous medium source and the analyzer are shown in cross section).

DETAILED DESCRIPTION OF THE INVENTION

Now follows the description of a specific embodiment of the proposed device for introducing particles into an analyzer 1 of dustiness of a gaseous medium. Referring to the drawing, the device comprises a cell 2 in whose bottom 3 there is provided a vertical feed duct 4 having two portions of different cross-sectional areas. The wider portion of the duct 4 is coupled by a threaded connection to a nozzle 5 of the analyzer 1. The cell 2 has a transparent cover 6 above which a microscope 7 is positioned. Made in a wall 8 of the cell 2 is a through guide duct 9 having two portions of different cross-sectional areas. The wider portion of the duct 9 is coupled by a threaded connection to an inlet 10 of a source 11 of a pure gaseous medium. Also provided in the bottom 3 of the cell 2 is a horizontal channel 12 which is an extension of the duct 9 and intersects the duct 4. Inserted between the cover 6 and a body 13 of the cell 2 is a rubber sealing ring 14. For air-tightness of the coupling between the cell 2 and the nozzle 5 of the analyzer 1, a rubber sealing ring 15 is placed on the body 13 of the cell 2. The inner surfaces of the duct 4 and the channel 12 have an antiadhesive coating 16.

The proposed device for introducing particles into an analyzer of dustiness of a gaseous medium operates as follows.

Shaken off, e.g. a needle, into the horizontal channel 12 of the cell 2 are particles of a material, having a particular shape and size. The cell 2 is then closed by the transparent cover 6, and the number of particles in the cell, equal to $n_1$, is counted with the aid of the microscope 7. A flow of pure gaseous medium, e.g. purified air, supplied under pressure from the source 11 into the horizontal channel 12 via the through guide duct 9, entrains the particles and transports them via the vertical feed duct 4 into the nozzle 5 of the analyzer 1. At the same time, the duct 4 focuses the particle flow axially with respect to the nozzle 5 of the analyzer 1. The entrainment of particles is observed through the microscope 7, the source 11 is disconnected, and the number $n_2$ of particles remaining in the channel 12 is counted.

Then, the reading of the analyzer 1, indicating the number $n_3$ of particles passed thereinto, is taken.

The obtained data permit determining error $\delta$ of counting particles by the analyzer 1, using the following formula:

$$\delta = [(n_1 - n_2) - n_3/n_3]100\%.$$

The present invention permits simplifying the procedure of calibrating analyzers of dustiness of a gaseous medium.

In addition, the invention enhances the accuracy of counting particles by analyzers of dustiness of a gaseous medium.

What is claimed is:

1. A device for introducing a determinable quantity of particles into an analyzer of dustiness of a gaseous medium, the particles being used to calibrate the analyzer, said device comprising:
   a cell having a wall, a bottom and a transparent cover;
   a through guide duct made in said wall of said cell;
   a vertical feed duct made in said bottom of said cell, intended for communication with the analyzer and having an inner surface;
   a horizontal channel made in said bottom of said cell, which is an extension of said through guide duct, intersects said vertical feed duct, and has an inner surface, said horizontal channel receiving particles to be sensed by an analyzer being calibrated;
   a microscope arranged above said transparent cover of said cell; and
   a source of a pure gaseous medium, intended for supplying said pure gaseous medium under pressure and having an outlet communicating with said through guide duct.

2. A device as claimed in claim 1, wherein said inner surfaces of said horizontal channel and said vertical feed duct have an antiadhesive coating.

3. A device as claimed in claim 1 or 2, wherein said transparent cover is removable from said cell so that particles to be sensed can be placed in said horizontal channel, the portion of said horizontal channel receiving the impurities being viewable through said microscope.

* * * * *